(12) United States Patent
Brereton et al.

(10) Patent No.: US 9,358,345 B2
(45) Date of Patent: Jun. 7, 2016

(54) AUTO-INJECTOR

(75) Inventors: Simon Francis Brereton, Cambridge (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 483 days.

(21) Appl. No.: 13/876,796

(22) PCT Filed: Oct. 6, 2011

(86) PCT No.: PCT/EP2011/067497
§ 371 (c)(1),
(2), (4) Date: Aug. 12, 2013

(87) PCT Pub. No.: WO2012/045834
PCT Pub. Date: Apr. 12, 2012

(65) Prior Publication Data
US 2013/0317450 A1    Nov. 28, 2013

Related U.S. Application Data

(60) Provisional application No. 61/432,259, filed on Jan. 13, 2011.

(30) Foreign Application Priority Data

Oct. 8, 2010   (EP) ..................................... 10187000

(51) Int. Cl.
*A61M 5/31* (2006.01)
*A61M 5/315* (2006.01)
*A61M 5/20* (2006.01)

(52) U.S. Cl.
CPC ......... *A61M 5/31581* (2013.01); *A61M 5/2033* (2013.01); *A61M 2005/206* (2013.01); *A61M 2005/2013* (2013.01); *A61M 2205/581* (2013.01); *A61M 2205/582* (2013.01)

(58) Field of Classification Search
CPC ............... A61M 2005/2013; A61M 2005/206; A61M 2205/581; A61M 2205/582; A61M 5/2033; A61M 5/31581
See application file for complete search history.

(56) References Cited

U.S. PATENT DOCUMENTS 2,591,457 A    4/1952  Maynes
5,026,349 A    6/1991  Schmitz et al.
(Continued)

FOREIGN PATENT DOCUMENTS

EP          1728529 A1    12/2006

*Primary Examiner* — Aarti B Berdichevsky
(74) *Attorney, Agent, or Firm* — Fish & Richardson P.C.

(57) ABSTRACT

The invention refers to a shuttering mechanism for controlling translation of a longitudinally moveable component within a housing, the shuttering mechanism comprising at least one fixed shutter attached to or integrated with the housing and at least one moving shutter arm moveable between at least one locking position and at least one unlocking position, wherein at least one resilient arm is associated with the longitudinally moveable component, the resilient arm having a dog resiliently biased towards the fixed shutter, wherein the moving shutter arm is arranged alongside the fixed shutter, wherein at least one fixed protrusion is arranged on the fixed shutter at least one of them arranged for engaging the dog so as to prevent translation of the longitudinally moveable component in a proximal direction, wherein at least one moving protrusion is arranged on the moving shutter arm, at least one of them ramped in a manner to disengage the dog from the at least one of the fixed protrusions and/or to prevent engagement of the dog to the fixed protrusion when the moving shutter arm is in the unlocking position, wherein the moving shutter arm is arranged to allow engagement of the dog with the fixed protrusion in the locking position.

16 Claims, 8 Drawing Sheets

(56) References Cited

U.S. PATENT DOCUMENTS

| | | | |
|---|---|---|---|
| 9,011,387 B2* | 4/2015 | Ekman | A61M 5/2033 604/197 |
| 9,155,837 B2* | 10/2015 | Kemp | A61M 5/2033 |
| 9,180,258 B2* | 11/2015 | Kemp | A61M 5/2033 |
| 2008/0262438 A1 | 10/2008 | Bollenbach et al. | |
| 2013/0096512 A1* | 4/2013 | Ekman | A61M 5/2033 604/197 |
| 2013/0131602 A1* | 5/2013 | Kemp | A61M 5/2033 604/197 |
| 2013/0138048 A1* | 5/2013 | Kemp | A61M 5/2033 604/196 |
| 2013/0138049 A1* | 5/2013 | Kemp | A61M 5/2033 604/197 |
| 2013/0150800 A1* | 6/2013 | Kemp | A61M 5/2033 604/192 |
| 2013/0190694 A1* | 7/2013 | Barrow-Williams | A61M 5/2033 604/198 |
| 2013/0204195 A1* | 8/2013 | Ekman | A61M 5/2033 604/197 |
| 2013/0204198 A1* | 8/2013 | Burnell | A61M 5/2033 604/197 |
| 2013/0261558 A1* | 10/2013 | Hourmand | A61M 5/2033 604/197 |
| 2013/0267909 A1* | 10/2013 | Hourmand | A61M 5/2033 604/197 |
| 2013/0274662 A1* | 10/2013 | Hourmand | A61M 5/2033 604/110 |
| 2013/0274666 A1* | 10/2013 | Brereton | A61M 5/2033 604/117 |
| 2013/0274671 A1* | 10/2013 | Jennings | A61M 5/20 604/154 |
| 2013/0296794 A1* | 11/2013 | Brereton | A61M 5/2033 604/197 |
| 2013/0296795 A1* | 11/2013 | Ekman | A61M 5/2033 604/197 |
| 2013/0296796 A1* | 11/2013 | Hourmand | A61M 5/2033 604/197 |
| 2013/0310744 A1* | 11/2013 | Brereton | A61M 5/2033 604/111 |
| 2013/0310757 A1* | 11/2013 | Brereton | A61M 5/3257 604/197 |
| 2013/0310759 A1* | 11/2013 | Hourmand | A61M 5/2033 604/198 |
| 2013/0317427 A1* | 11/2013 | Brereton | A61M 5/2033 604/111 |
| 2013/0317428 A1* | 11/2013 | Brereton | A61M 5/2033 604/111 |
| 2013/0317446 A1* | 11/2013 | Hourmand | A61M 5/2033 604/196 |
| 2013/0317479 A1* | 11/2013 | Brereton | A61M 5/2033 604/506 |
| 2013/0324924 A1* | 12/2013 | Brereton | A61M 5/2033 604/110 |
| 2013/0324925 A1* | 12/2013 | Brereton | A61M 5/2033 604/110 |
| 2013/0324935 A1* | 12/2013 | Brereton | A61M 5/2033 604/198 |
| 2013/0324938 A1* | 12/2013 | Brereton | A61M 5/2033 604/218 |
| 2014/0135705 A1* | 5/2014 | Hourmand | A61M 5/2033 604/196 |

* cited by examiner

AUTO-INJECTOR

CROSS REFERENCE TO RELATED APPLICATIONS

The present application is a U.S. National Phase Application pursuant to 35 U.S.C. §371 of International Application No. PCT/EP2011/067497 filed Oct. 6, 2011, which claims priority to European Patent Application No. 10187000.4 filed Oct. 8, 2010 and U.S. Provisional Patent Application No. 61/432,259 filed Jan. 13, 2011. The entire disclosure contents of these applications are herewith incorporated by reference into the present application.

FIELD OF INVENTION

The invention relates to a shuttering mechanism for controlling translation of a longitudinally moveable component within an elongate housing, in particular for application in an auto-injector for delivering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, handshaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, energy stored in the tension spring is released and the injection needle is automatically retracted back to its original storage position.

SUMMARY

It is an object of the present invention to provide a novel means for controlling translation of a longitudinally moveable component within an elongate housing, e.g. movement of a plunger within the housing of an auto-injector.

The object is achieved by a shuttering mechanism according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention a shuttering mechanism for controlling translation of a longitudinally moveable component within a housing comprises at least one fixed shutter attached to or integrated with the housing and at least one moving shutter arm moveable between at least one locking position and at least one unlocking position. At least one resilient arm is associated with the longitudinally moveable component. The resilient arm has a dog resiliently biased towards the fixed shutter. The moving shutter arm is arranged alongside the fixed shutter. At least one fixed protrusion is arranged on or comprised in the fixed shutter, at least one of the fixed protrusions arranged for engaging the dog so as to prevent translation of the longitudinally moveable component in the proximal direction. At least one moving protrusion is arranged on the moving shutter arm, at least one of the moving protrusions ramped in a manner to disengage the dog from the at least one of the fixed protrusions and/or to prevent engagement of the dog to the fixed protrusion when the moving shutter arm is in the unlocking position. The moving shutter arm is arranged to allow engagement of the dog with the fixed protrusion in the locking position. The ramps of the ramped moving protrusions are arranged to directly or indirectly push the dog away from behind or between the fixed protrusions upon translation of the moving shutter arm into the unlocked position.

The shuttering mechanism according to the invention combines increased functionality with a particularly low part count.

The moving shutter arm may be arranged to be translated in longitudinal direction between its locking position and its unlocking position in which case the ramp of the fixed protrusion faces in either the proximal or the distal direction. Alternatively the moving shutter arm may be arranged to be rotated between its locking position and its unlocking position.

In one embodiment of the invention a set of consecutive fixed protrusions, spaced from each other, is arranged on the fixed shutter, wherein a set of consecutive moving protrusions, spaced from each other, is arranged on the moving shutter arm, wherein both sets have the same pitch. This allows for stopping or pausing the translation of the longitudinally moveable component, e.g. a plunger for transferring a drive force from a drive means to a syringe or stopper in an auto-injector. In the locking position the moving protrusions are essentially in phase with the fixed protrusions thus allowing the dog of the resilient arm to catch between or behind the fixed protrusions. In the unlocking position the moving protrusions are out of phase with the fixed protrusions in such a manner that the moving protrusions prevent the dog from engaging with the fixed protrusions or disengage them so the dog of the resilient arm may travel along the surface created by the fixed and the moving protrusions without catching behind the fixed protrusions. This allows translation of the longitudinally moveable component. The translation is stopped by moving the moving shutter arm into the locking position, where the sets of fixed protrusions and moving protrusions are in phase so the dog can be caught between the fixed protrusions.

All moving protrusions may be ramped with their ramps facing in one direction. This allows for restarting a paused translation in the same manner as the initial start of the translation by camming the dog out of the space between the fixed protrusions. Pausing and restarting may be desirable in an auto-injector if the user is finding the injection too fast or painful. Furthermore an injection may be prematurely halted without releasing the entire dose of medicament in the auto-injector.

The ramp of the most distal moving protrusion may be longer than the ramps of the other moving protrusions. Hence, camming the dog from its position prior to use requires more travel of the moving shutter than for restarting the injection.

In another embodiment the ramp of the most distal ramped moving protrusion may be steeper than the ramps of the other ramped moving protrusions. Consequently, camming the dog from its position prior to use requires more force on the moving shutter than for restarting the injection.

In one embodiment all fixed protrusions may be arranged as castellations, i.e. blocks with rectangular edges. This allows for catching the dog behind both edges so translation of the longitudinally moveable component in proximal direction can be stopped or paused and translation in distal direction is prevented if the shutters are out of phase. Furthermore, in the embodiment with castellations as fixed protrusions and ramped moving protrusions the dog running along the surface will produce a sound each time it snaps off the top of the fixed shutter castellation and will alternately apply a force to the moving shutter arm as it rides up the ramps of the moving protrusions. This will provide both audible and tactile feedback that the translation, e.g. an injection is taking place. Once these stop, the translation is complete.

In another embodiment a most distal moving protrusion may be ramped, wherein the other moving protrusions are arranged as castellations. Hence, the translation, once stopped cannot be restarted. This embodiment does not produce an audible or tactile feedback during the translation.

In yet another embodiment all fixed protrusions may be ramped with their ramps facing in the opposite (proximal) direction of the moving protrusion's ramps. If the shutters are out of phase, the dog will ride up and down the surface formed by the out of phase fixed shutter and moving shutter arm. The dog running along the surface will provide both audible and tactile feedback that the injection is taking place, but muffled in comparison to the embodiment with the castellation on the fixed shutter. The translation can be interrupted and restarted. Furthermore, the ramped fixed protrusions in place of the castellations allow for implementing a retraction of the longitudinally moveable component, e.g. retraction of a plunger, syringe and needle of an auto-injector.

In an alternative embodiment a set of consecutive fixed protrusions, spaced from each other, is arranged on the fixed shutter. The most distal fixed protrusion is arranged as a castellation and the other fixed protrusions ramped with their ramps facing in distal direction. This embodiment does not allow stopping or pausing the injection but gives an audio feedback.

In an alternative embodiment a set of consecutive fixed protrusions in the shape of castellations, spaced from each other and protruding to one side (towards the dog), is arranged on the fixed shutter. The moving shutter arm has at least one (preferably more than one) ramped moving protrusion protruding to the opposite side. The ramp of the ramped moving protrusion is engageable with a respective mating ramp in the fixed shutter, such that a backside of the moving shutter arm can become flush with a top of the fixed protrusions on relative motion of the moving shutter arm relative to the fixed shutter arm so as to disengage the dog from the fixed shutter or prevent them from re-engaging.

In the embodiments which allow stopping and/restarting the injection, there will always be an amount of liquid medicament dispensed before the injection actually stops since the dog has to travel until the distal edge of the next fixed protrusion. In order to reduce this amount of medicament the auto-injector may have at least two fixed shutters and at least two moving shutters arranged as pairs with the pitches of the pairs out of phase with each other. Thus, the effective pitch of the shutter mechanism would be halved and the dispensed dose of medicament until the stop would be significantly reduced.

The shuttering mechanism is preferably applied in an auto-injector for administering a dose of a liquid medicament, the auto-injector having a distal end and a proximal end with an orifice intended to be applied against an injection site and comprising:

an elongate housing arranged to contain a syringe with a hollow needle and a stopper for sealing the syringe and displacing the medicament, wherein the syringe is slidably arranged with respect to the housing, a drive means capable of, upon activation:

pushing the needle from a retracted position into an advanced position through the orifice and past the proximal end, and operating the syringe to supply the dose of medicament, a plunger for transmitting power from the drive means to the syringe and/or stopper, and activating means arranged to lock the drive means in a compressed state prior to manual operation and capable of, upon manual operation, releasing the drive means for injection.

The shuttering mechanism is arranged as the activating means and for controlling translation of the plunger being the longitudinally moveable component. The resilient arm of the shuttering mechanism is a plunger arm attached to the plunger.

In one embodiment the shutter arm is connected to a sheath, telescoped within the proximal end of the housing and arranged to protrude proximally from the housing at least in an initial position in an as delivered state of the auto-injector. In the initial position of the sheath the shutter arm is in the locking position. From the initial position the sheath may be translated in distal direction into a triggering position thereby shifting the shutter arm into the unlocking position. This occurs when the user presses the proximal end of the auto-injector against an injection site, i.e. the skin of a patient. Thus the dog of the plunger arm comes clear of the castellations and the plunger is translated under load of the drive means so needle insertion and injection can take place. Removal of the auto-injector from the injection site can be used to stop injection and/or to trigger further actions of the auto-injector such as needle retraction.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
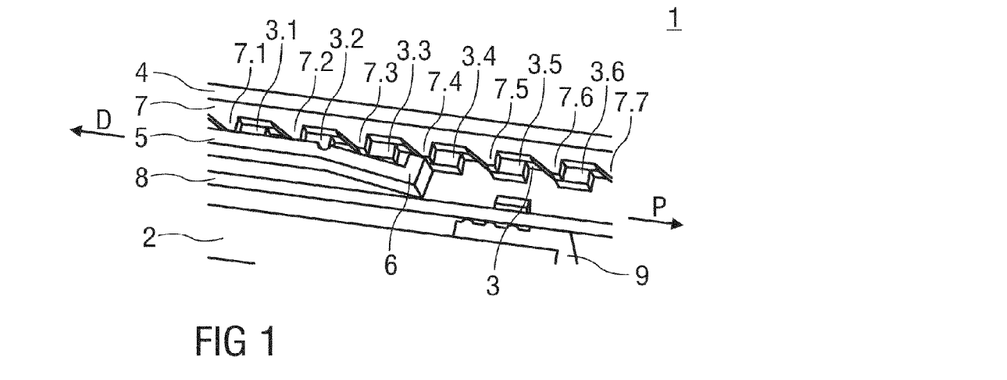
FIG. 1 is a detail view of a first embodiment of a shuttering mechanism in an auto-injector.

FIG. 1 shows a shuttering mechanism 1 for controlling translation of a longitudinally moveable component 2. The shuttering mechanism 1 comprises at least one fixed shutter 3 having set of fixed protrusions 3.1 to 3.6 in the shape of castellations 3.1 to 3.6, the fixed shutter 3 preferably being part of a housing 4 or chassis. The shuttering mechanism 1 furthermore comprises at least one resilient arm 5 associated with the longitudinally moveable component 2. At a proximal tip of the resilient arm 5 a dog 6 is resiliently biased towards the castellations 3.1 to 3.6 so as to engage between or behind the castellations 3.1 to 3.6 and block the translation of the longitudinally moveable component 2. A respective moving shutter arm 7 is arranged alongside the fixed shutter 3, the moving shutter arm 7 having a number of consecutive ramped moving protrusions 7.1 to 7.6 spaced from each other, their ramps facing in distal direction D. The castellations 3.1 to 3.6 and the ramped protrusions 7.1 to 7.6 have the same pitch and form a profiled surface. The moving shutter arm 7 is moveable in longitudinal direction with respect to the fixed shutter 3. The moving shutter arm 7 has at least one locking position with its ramped protrusions 7.1 to 7.6 essentially in phase with the castellations 3.1 to 3.6 thus allowing the dog 6 of the resilient arm 5 to catch between or behind the castellations 3.1 to 3.6. The moving shutter arm 7 has at least one unlocking position with its ramped protrusions 7.1 to 7.6 out of phase with the castellations 3.1 to 3.6 in such a manner that the ramped protrusions 7.1 to 7.6 prevent the dog 6 from engaging with the castellations 3.1 to 3.6 or disengage them thus allowing translation of the longitudinally moveable component 2.

Figure 15:
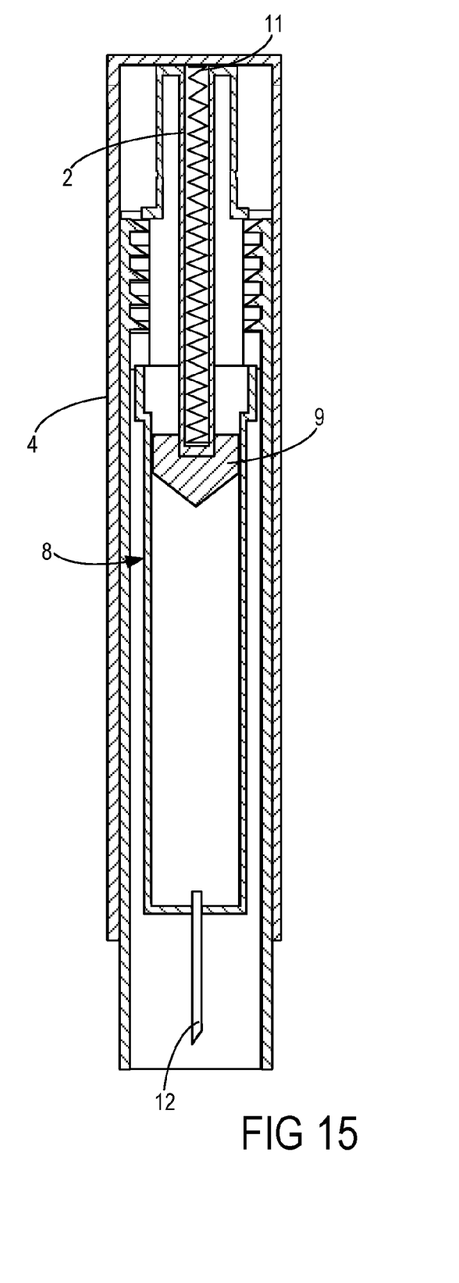
FIG. 15 is a schematic cross-sectional side view of an example of an auto-injector.

Referring also to an example of an auto-injector depicted in FIG. 15, the longitudinally moveable component 2 is preferably a plunger 2 for transmitting a driving force of a drive means, e.g. a spring 11 (as depicted in FIG. 15) to a syringe 8 or to a stopper 9 for sealing the syringe 8 and displacing a liquid medicament from the syringe 8. The syringe 8, the shuttering mechanism 1, the plunger 2 and the drive means may be part of an auto-injector for delivering the medicament.

FIG. 1 shows the shuttering mechanism 1 during an injection.

Prior to use the plunger 2 resolves the driving force acting in proximal direction P into the fixed shutter 3. The moving shutter arm 7 is in phase with the fixed shutter 3 and hence carries no load. The plunger 2 cannot be pushed in proximal direction P because of the dog 6 caught behind the most distal castellation 3.1.

To allow translation of the plunger 2 in proximal direction P, the moving shutter arm 7 must be translated in distal direction D relative to the fixed shutter 3, such that they are out of phase. The ramp of the most distal moving protrusion 7.1 of the moving shutter arm 7 cams the dog 6 out of engagement with the fixed shutter 3, to the same level as the top of the first castellation 3.1. At this point the plunger 2 is free to move in proximal direction P under the driving force. If the relative position of the shutters 3, 7 is held constant, the dog 6 will continue to ride up the surface formed by the out of phase fixed shutter 3 and moving shutter arm 7 in proximal direction P as shown in FIG. 1.

Figure 2:
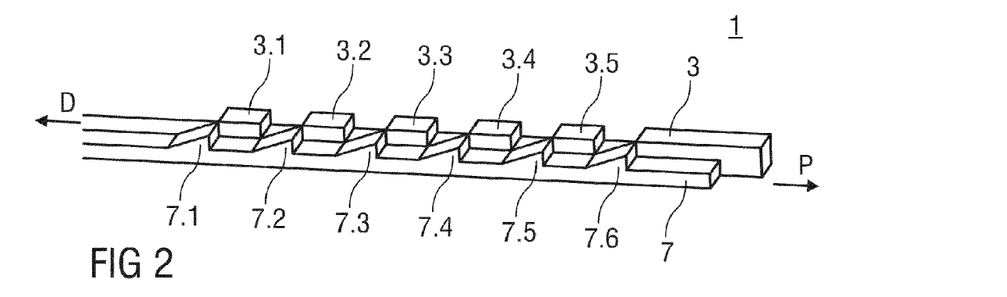
FIG. 2 is a schematic view of the shuttering mechanism of FIG. 1 with a moving shutter arm with ramped moving protrusions.

In the embodiment shown in FIGS. 1 and 2 the dog 6 running along the surface will produce a sound each time it snaps off the top of the fixed shutter 3 castellation 3.1 to 3.6 and will alternately apply a force to the moving shutter arm 7 as it rides up the ramps of the moving protrusions 7.1 to 7.6. This will provide both audible and tactile feedback that the injection is taking place. Once these stop, the injection is complete.

If the moving shutter arm 7 is translated back in phase with the fixed shutter 3 during the injection (either by moving it further in distal direction D, or moving it towards the position it was prior to firing), the dog 6 will catch on the next fixed shutter 3 castellation 3.1 to 3.6 and stop the injection. The injection can then be restarted by translating the moving shutter arm 7 in phase with the fixed shutter 3 again. Alternatively the moving shutter arm 7 may be latched or disconnected from the user's control, preventing any further dose from being delivered.

Figure 3:
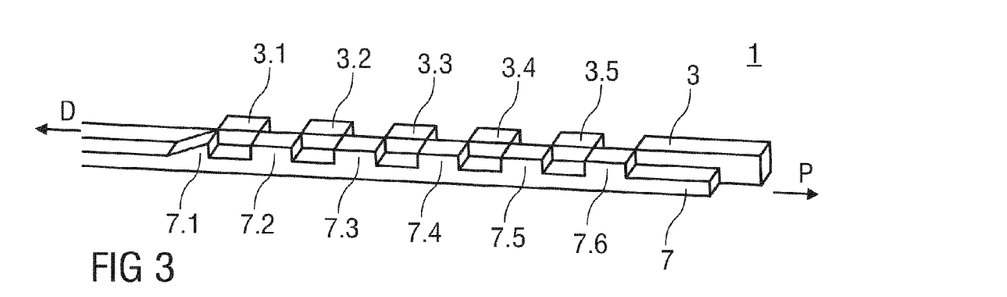
FIG. 3 is a schematic view of a second embodiment of the shuttering mechanism.

FIG. 3 shows an alternative embodiment of the shuttering mechanism 1. The moving shutter arm 7 has only one ramped moving protrusion 7.1 while the other moving protrusions 7.2 to 7.6 are castellations. If the moving shutter arm 7 is translated in phase with the fixed shutter 3 during translation of the plunger 2, the dog 6 will flex into the next space between the castellations 3.1 to 3.5, 7.1 to 7.6 and remain there since it cannot be ramped out by the moving shutter arm 7, again. Hence, the injection, once stopped cannot be restarted. The embodiment of FIG. 3 does not produce an audible or tactile feedback during the translation of the plunger 2, e.g. during injection.

Figure 4:
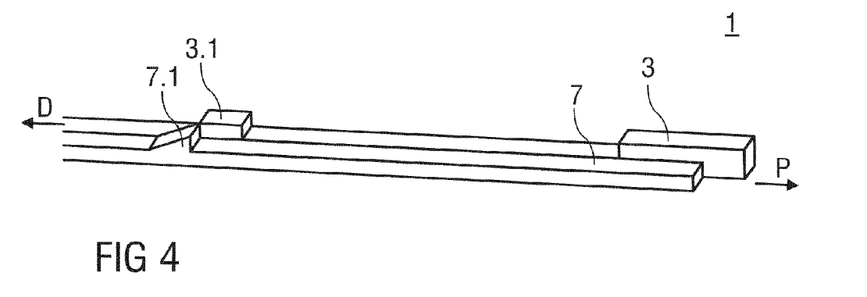
FIG. 4 is a schematic view of a third embodiment of the shuttering mechanism.

FIG. 4 shows another embodiment of the shuttering mechanism 1 wherein only one fixed castellation 3.1 is provided on the fixed shutter 3 and only one ramped moving protrusion 7.1 on the moving shutter arm 7. To allow translation of the plunger 2 in proximal direction P, the moving shutter arm 7 must be translated in distal direction D relative to the fixed shutter 3, such that they are out of phase as in FIG. 4. The ramp of the moving protrusion 7.1 cams the dog 6 out of engagement with the fixed shutter 3, to the same level as the top of the fixed castellation 3.1. At this point the plunger 2 is free to move in proximal direction P under the driving force. From this point on the injection continues without the user being able to pause or stop it. The embodiment of FIG. 4 does not produce an audible or tactile feedback during the translation of the plunger 2, e.g. during injection.

Figure 5:
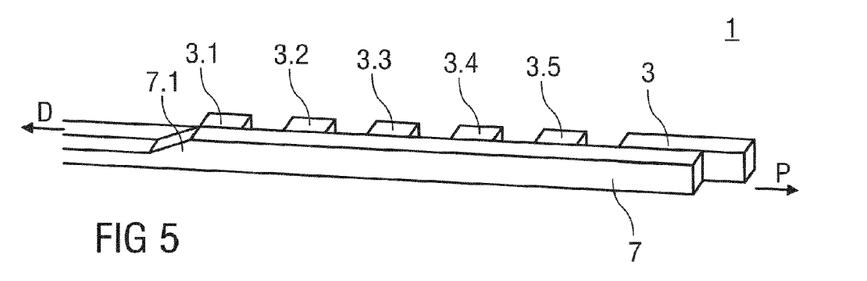
FIG. 5 is a schematic view of a fourth embodiment of the shuttering mechanism.

FIG. 5 is an embodiment of the shuttering mechanism wherein a set of castellations 3.1 to 3.5 is provided on the fixed shutter 3 and only one ramp 7.1 on the moving shutter arm 7. Proximally from that ramp 7.1 the moving shutter arm 7 remains on the top level of the ramp 7.1. To allow translation of the plunger 2 in proximal direction P, the moving shutter arm 7 must be translated in distal direction D relative to the fixed shutter 3, such that they are out of phase as in FIG. 5. The ramp 7.1 of the moving shutter arm 7 cams the dog 6 out of engagement with the fixed shutter 3, to the same level as the top of the castellation 3.1. At this point the plunger 2 is free to move in proximal direction P under the driving force. From this point on the injection continues without the user being able to pause or stop it. The embodiment of FIG. 5 does not produce an audible or tactile feedback during the translation of the plunger 2, e.g. during injection. This embodiment allows for using the same housing 4 with the integrated fixed shutter 3 as in the embodiment of FIGS. 1 and 2. The functionality is changed just by applying the modified moving shutter arm 7. This allows for creating a platform of autoinjectors with a number of common parts, where only some parts have to be exchanged in order to change the functionality.

Figure 6:
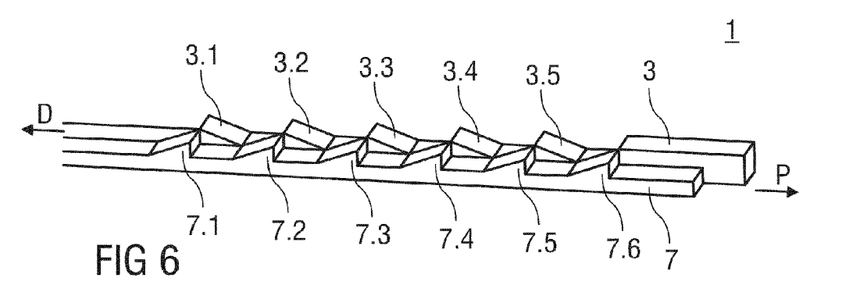
FIG. 6 is a schematic view of a fifth embodiment of the shuttering mechanism.

FIG. 6 is yet another embodiment of the shuttering mechanism 1. The shuttering mechanism 1 comprises at least one fixed shutter 3 in the shape of a set of ramped moving protrusions 3.1 to 3.5. The ramps of the ramped fixed protrusions 3.1 to 3.5 of the fixed shutter 3 face in proximal direction P. A respective moving shutter arm 7 is arranged alongside the fixed shutter 3, the moving shutter arm 7 having a number of consecutive ramped fixed protrusions 7.1 to 7.6 spaced from each other, their ramps facing in distal direction D. The ramped fixed protrusions 3.1 to 3.5 of the fixed shutter 3 and the ramped moving protrusions 7.1 to 7.6 of the moving shutter arm 7 have the same pitch and form a profiled surface. The moving shutter arm 7 is moveable in longitudinal direction with respect to the fixed shutter 3. The moving shutter arm 7 has at least one locking position with its ramped moving protrusions 7.1 to 7.6 essentially in phase with the ramped fixed protrusions 3.1 to 3.5 of the fixed shutter 3 thus allowing the dog 6 of the resilient arm 5 to catch between or behind the ramped fixed protrusions 3.1 to 3.5 of the fixed shutter 3. The moving shutter arm 7 has at least one unlocking position with its ramped moving protrusions 7.1 to 7.6 out of phase with the ramped fixed protrusions 3.1 to 3.5 in such a manner that the ramped moving protrusions 7.1 to 7.6 prevent the dog 6 from engaging with the ramped fixed protrusions 3.1 to 3.5 or disengage them thus allowing translation of the longitudinally moveable component 2.

Prior to use the plunger 2 resolves the driving force acting in proximal direction P into the fixed shutter 3. The moving shutter arm 7 is in phase with the fixed shutter 3 and hence carries no load. The plunger 2 cannot be pushed in proximal direction P because of the dog 6 caught behind the most distal ramped fixed protrusion 3.1 of the fixed shutter 3.

To allow translation of the plunger 2 in proximal direction P, the moving shutter arm 7 must be translated in distal direction D relative to the fixed shutter 3, such that they are out of phase. The ramp of the most distal ramped fixed protrusion 7.1 of the moving shutter arm 7 cams the dog 6 out of engagement with the fixed shutter 3, to the same level as the top of the ramped fixed protrusion 3.1. At this point the plunger 2 is free to move in proximal direction P under the driving force. If the relative position of the shutters 3, 7 is held constant, the dog 6 will continue to ride up and down the surface formed by the out of phase fixed shutter 3 and moving shutter arm 7.

Figure 7:
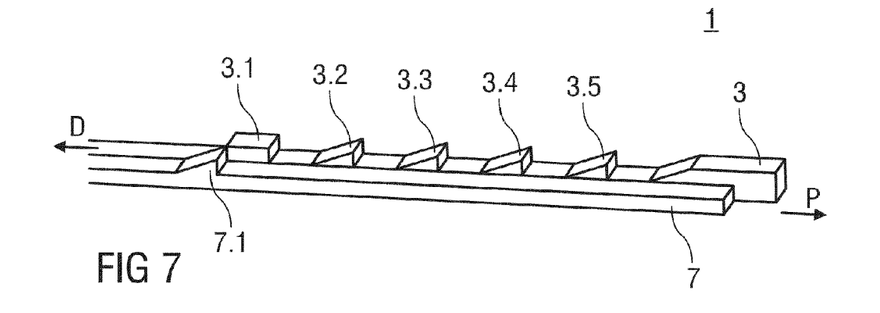
FIG. 7 is a schematic view of a sixth embodiment of the shuttering mechanism.

In the embodiment shown in FIG. 7 the dog 6 running along the surface will provide both audible and tactile feedback that the injection is taking place, but muffled in comparison to the embodiment of FIG. 1.

As in the embodiment of FIG. 1 the injection can be interrupted and restarted. Furthermore, the ramped fixed protrusions 3.1 to 3.5 of the fixed shutter 3 in place of the castellations allow for implementing a retraction of the plunger 2 and consequently retraction of the syringe 8 and needle (e.g., a needle 12 of the syringe 8 shown in FIG. 15), since as the fixed shutter 3 and the moving shutter arm 7 are out of phase as in FIG. 6, the dog 6 can run in distal direction D as well without catching between the ramped protrusions 3.1 to 3.5, 7.1 to 7.6 of either shutter 2.3, 10.2.

FIG. 7 is another embodiment of the shuttering mechanism 1. The shuttering mechanism 1 comprises at least one fixed shutter 3 with a set of fixed protrusions 3.1 to 3.5, the most distal one of them in the shape of a castellation 3.1 and the other protrusions 3.2 to 3.5 ramped with their ramps facing in distal direction D. A moving shutter arm 7 is arranged alongside the fixed shutter 3, the moving shutter arm 7 having one ramped protrusion 7.1 with its ramp facing in distal direction D. The moving shutter arm 7 is moveable in longitudinal direction with respect to the fixed shutter 3.

Prior to use the plunger 2 resolves the driving force acting in proximal direction P into the fixed castellation 3.1 of the fixed shutter 3. The ramped moving protrusion 7.1 of the moving shutter arm 7 is in phase with the fixed castellation 3.1 of the fixed shutter 3. The plunger 2 cannot be pushed in proximal direction P because of dog 6 caught behind the fixed castellation 3.1 of the fixed shutter 3.

To allow translation of the plunger 2 in proximal direction P, the moving shutter arm 7 must be translated in distal direction D relative to the fixed shutter 3, such that they are out of phase. The ramp of the ramped moving protrusion 7.1 cams the dog 6 out of engagement with the fixed shutter 3, to the same level as the top of the first fixed protrusion 3.1. At this point the plunger 2 is free to move in proximal direction P under the driving force. From this point on the injection continues without the user being able to pause or stop it. The dog 6 will continue to ride up and down the surface formed by the fixed protrusions 3.2 to 3.5.

In the embodiment shown in FIG. 7 the dog 6 running along the surface will provide only an audible feedback that the injection is taking place. If the moving shutter 7 had ramped protrusions 7.2 to 7.6 and the fixed shutter 3 had none, the shuttering mechanism 1 could also provide a tactile feedback.

Figure 8A:
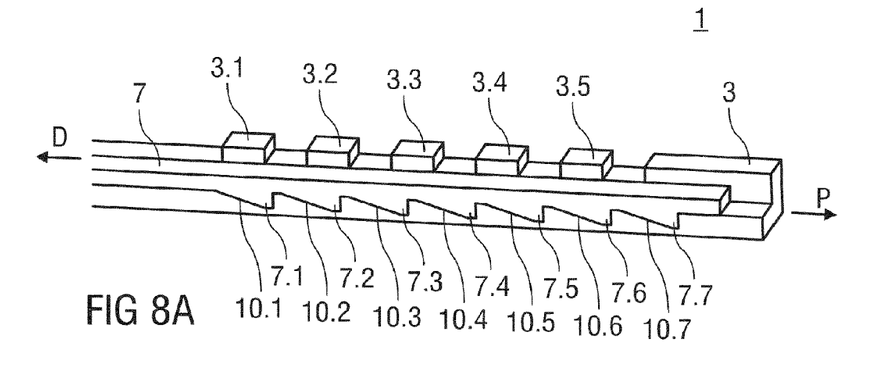
FIG. 8a is a schematic view of a seventh embodiment of the shuttering mechanism prior to actuation.
Figure 8B:
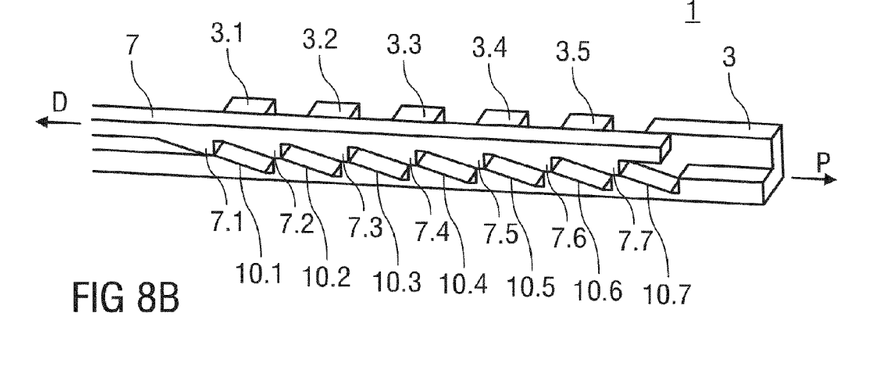
FIG. 8b is a schematic view of the seventh embodiment of the shuttering mechanism during translation.

FIGS. 8a and 8b show yet another embodiment of the shuttering mechanism 1.

The shuttering mechanism 1 comprises at least one fixed shutter 3 with a set of fixed protrusions 3.1 to 3.5 in the shape of castellations protruding to one side. A moving shutter arm 7 is arranged alongside the fixed shutter 3, the moving shutter arm 7 having ramped moving protrusions 7.1 to 7.7 protruding to the opposite side with their ramps facing in distal direction D and engaged with mating ramps 10.1 to 10.7 in the fixed shutter 3. The moving shutter arm 7 is moveable in longitudinal direction with respect to the fixed shutter 3.

Prior to use (see FIG. 8a) the plunger 2 resolves the driving force acting in proximal direction P into the fixed castellation 3.1 of the fixed shutter 3. The ramped moving protrusions 7.1 to 7.7 of the moving shutter arm 7 are fully engaged with the mating ramps 10.1 to 10.7 of the fixed shutter 3. The plunger 2 cannot be pushed in proximal direction P because of dog 6 caught behind the fixed castellation 3.1 of the fixed shutter 3.

To allow translation of the plunger 2 in proximal direction P, the moving shutter arm 7 must be translated in distal direction D relative to the fixed shutter 3. The engaged ramped moving protrusions 7.1 to 7.7 and the mating ramps 10.1 to 10.7 push the moving shutter arm 7 away from the fixed shutter 3 so that a backside of the moving shutter arm 7 opposite the protrusions 7.1 to 7.7 becomes flush with the top of the fixed protrusions 3.1 to 3.5 thus disengaging the dog 6 from the fixed shutter 3 (see FIG. 8b). At this point the plunger 2 is free to move in proximal direction P under the driving force. If the relative position of the shutters 3, 7 is held constant, the dog 6 will continue to ride up the surface formed by the fixed shutter 3 and moving shutter arm 7 in proximal direction P.

If the moving shutter arm 7 is translated back in proximal direction P, the moving shutter 7 is no longer forced away from the fixed shutter 3 and the ramped moving protrusions 7.1 to 7.7 and the mating ramps 10.1 to 10.7 fully re-engage. The dog 6 will catch on the next fixed shutter 3 castellation 3.1 to 3.6 and stop the injection. The injection can then be restarted by translating the moving shutter arm 7 in distal direction D again.

In the embodiment of FIGS. 8a and 8b the number of moving protrusions 7.1 to 7.7 and their pitch relative to the pitch of the fixed protrusions 3.1 to 3.5 is insignificant other than to define the amount of distal movement of moving shutter arm 7 required to start or stop the proximal movement of plunger 2. It would be sufficient to have one moving protrusion 7.1 and one mating ramp 10.1. However, at least two moving protrusions 7.1 to 7.7 and two mating ramps 10.1 to 10.7 will be more robust.

The embodiment of FIGS. 8a and 8b does not provide audio or tactile feedback. Because there is no requirement for phasing between the fixed shutter 3 and the moving shutter 7, the fixed protrusions 3.1 to 3.5 can be thin and close together resulting in a better resolution of stopping positions. Other than in the previously described embodiments, where the distance between the fixed protrusions 3.1 to 3.5 is driven by the length of the ramps, which is driven by the force/displacement specified to release the dog 6, in the embodiment of FIGS. 8a and 8b the ramps of the moving protrusions 7.1 to 7.7 are independent of the fixed protrusions 3.1 to 3.5. Hence, more, closely spaced fixed protrusions 3.1 to 3.n can be used for improving the resolution of stopping positions.

Figure 9:
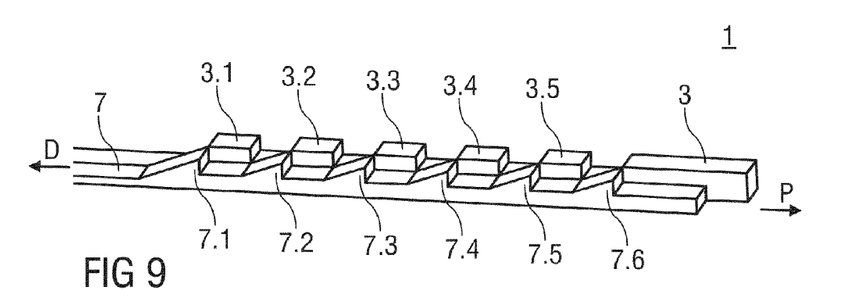
FIG. 9 is a schematic view of an eighth embodiment of the shuttering mechanism.
Figure 10:
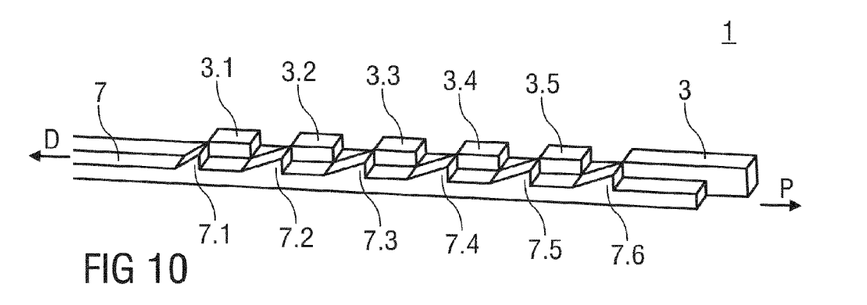
FIG. 10 is a schematic view of a ninth embodiment of the shuttering mechanism.
Figure 11:
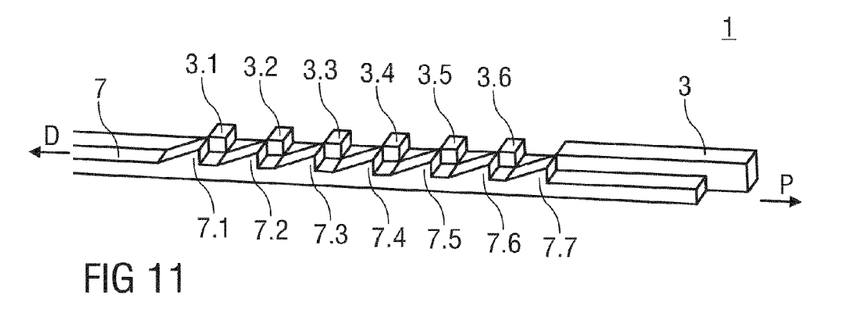
FIG. 11 is a schematic view of a tenth embodiment of the shuttering mechanism.
Figure 12A:
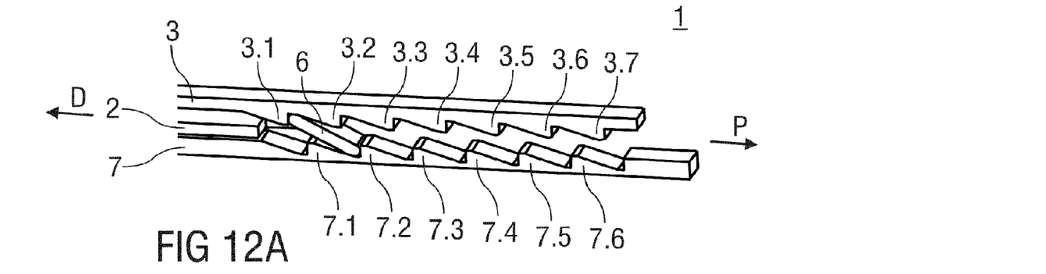
FIG. 12 is a schematic view of an eleventh embodiment of the shuttering mechanism.
Figure 12B:
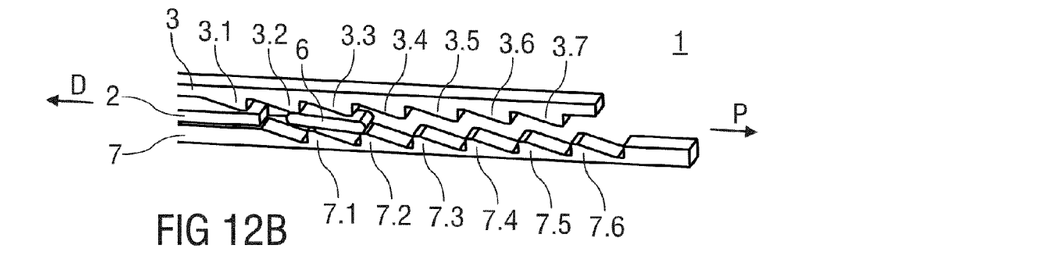
Figure 12C:
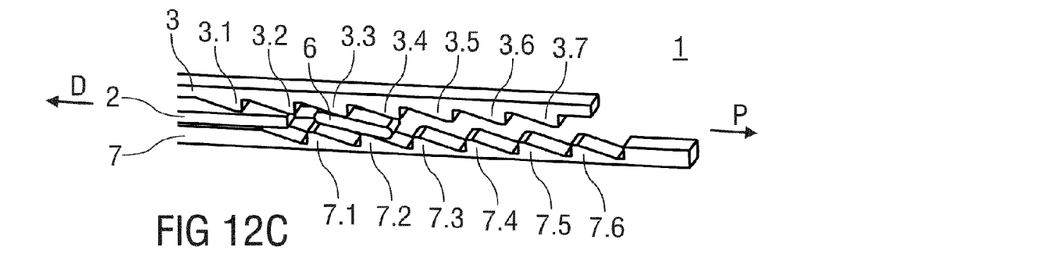
Figure 12D:
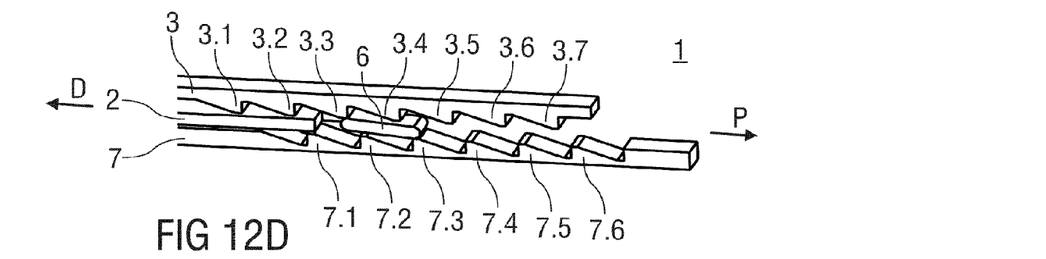

FIGS. 9, 10 and 11 show variants of the embodiment of FIGS. 1 and 2.

In FIG. 9, the level of the moving shutter arm 7 distally from the most distal ramped moving protrusion 7.1 as well as the level of the fixed shutter 3 distally from the most distal fixed protrusion 3.1 is below the level between the protrusions 3.1 to 3.5, 7.1 to 7.6. Consequently, the ramp of the ramped moving protrusion 7.1 is longer and camming the dog 6 from its position prior to use (distally from the protrusions 3.1, 7.1) requires more travel of the moving shutter 7 than for restarting the injection. This reduces the sensitivity of the arrangement to initial movement of the moving shutter arm 7, thereby reducing the chance of accidental triggering at the start of injection, yet maintains the ability to stop quickly. A good resolution between stopping points is provided.

In FIG. 10, the ramp of the most distal ramped moving protrusion 7.1 is steeper than the ramps of the other ramped moving protrusions 7.2 to 7.6. Consequently, camming the dog 6 from its position prior to use (distally from the protrusions 3.1, 7.1) requires more increased force on the moving shutter 7 than for restarting the injection. This reduces the chance of unintended triggering at the start of injection.

In the embodiments which allow stopping and/restarting the injection, there will always be an amount of liquid medicament dispensed before the injection actually stops since the dog 6 has to travel until the distal edge of the next fixed protrusion 3.1 to 3.5. In order to reduce this amount of medicament the auto-injector may have at least two shuttering mechanisms 1 (e.g. one on either side of the auto-injector) which are out of phase with each other. Thus, the effective pitch of the shutter mechanism 1 would be halved and the dispensed dose of medicament until the stop would be significantly reduced.

In FIG. 11, the fixed protrusions 3.1 to 3.6 and the moving protrusions 7.1 to 7.7 have different length. In order to control translation of the plunger 2 it is sufficient to cover the proximal edge of the moving protrusions 7.1 to 7.7 by the fixed protrusions 3.1 to 3.6. Complete overlap is not required. This allows the pitch of the shutters to be reduced so less medicament will be dispensed when the injection is interrupted. In this arrangement, the width of dog 6 in the axial direction needs to be sufficiently short that it will engage between the proximal edge of moving protrusion 7.1 to 7.7 and the distal edge of fixed protrusion 3.1 to 3.6 when the moving shutter arm 7 is moved out of phase with the fixed shutter 3.

The shuttering mechanism 1 may likewise be applied in other environments requiring control of translation of a longitudinally moveable component 2 other than a plunger 2.

The numbers of fixed protrusions 3.1 to 3.6 and moving protrusions 7.1 to 7.7 can differ from the numbers given in the embodiments.

Preferably, motion of the moving shutter arm 7 can be actuated by pressing a proximal end of an auto-injector against an injection site, e.g. a user's skin thereby pushing a sleeve or bar protruding from the proximal end of the auto-injector in distal direction. The motion may likewise be actuated by pushing an end button or indirectly through a cam or other mechanism linked to a side button or end button.

In addition, the auto-injector could be triggered by a secondary mechanism and the shuttering mechanism 1 could simply be used as a control mechanism. In this implementation, the moving shutter's 7 position would be controlled by a 'pause' button. This would separate the mechanisms to fire and pause the auto-injector, improving usability.

The 'pause' button could be designed to be 'press to inject' or 'press to pause'. The trigger could be combined with the pause button if the mechanism were 'press to inject'.

In an alternative embodiment the moving shutter 7 may be arranged to rotate or translate in the direction perpendicular to the shutters into the gaps between the fixed protrusions 3.1 to 3.5 rather than translated longitudinally as in the illustrated embodiments.

In yet another alternative embodiment, shown in FIG. 12, the shutters 3, 7 could be facing each other and the plunger 2 could navigate a gap created between the shutters 3, 7. For this arrangement, the distal faces of the fixed protrusions 3.1 to 3.5 and moving protrusions 7.1 to 7.6 both need to be ramped in order to allow the dog 6 to pass along the passage formed when the protrusions are moved out of phase.

Figure 13A:
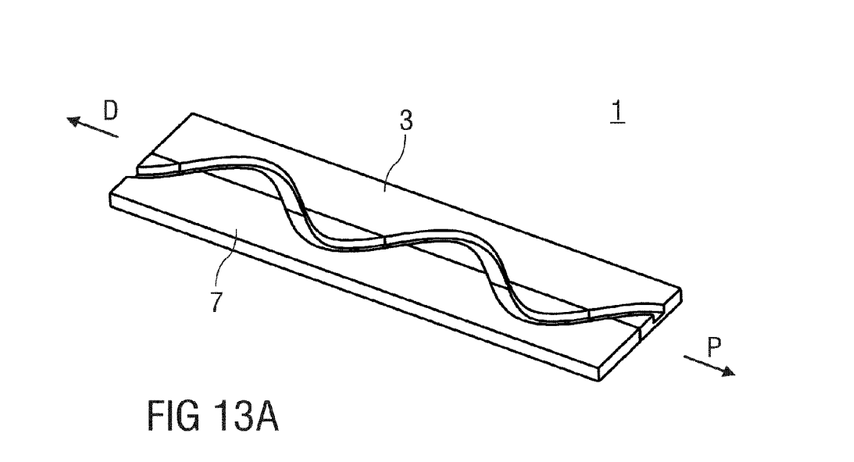
FIG. 13 is a schematic view of a twelfth embodiment of the shuttering mechanism.
Figure 13B:
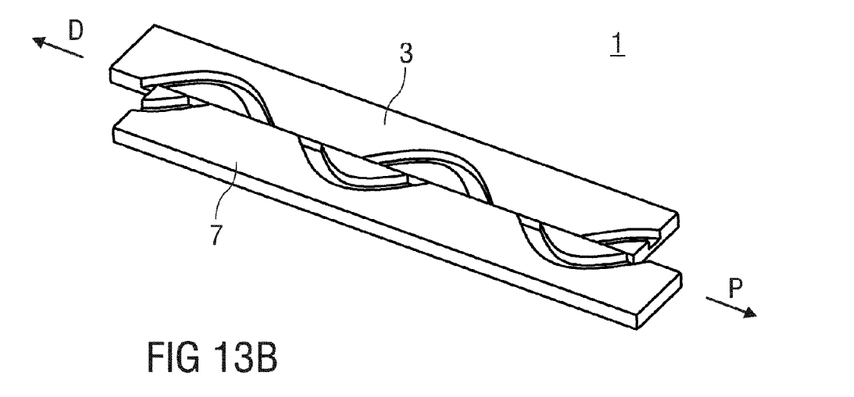
Figure 14A:
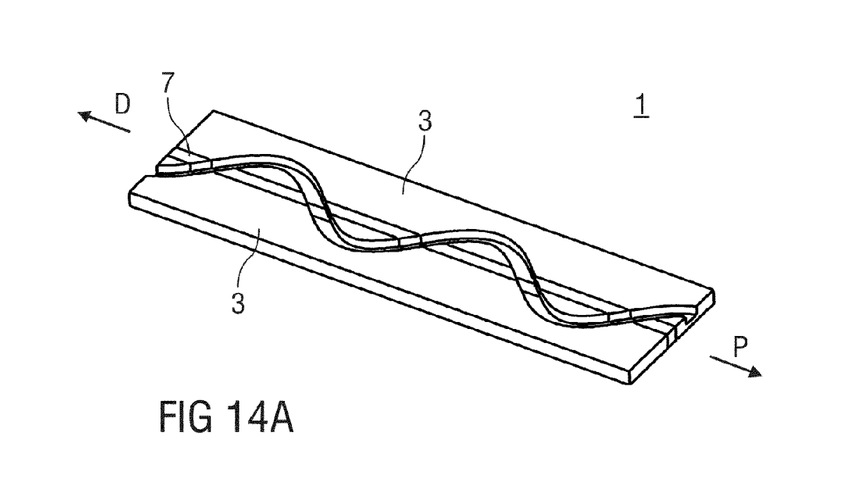
FIG. 14 is a schematic view of thirteenth embodiment of the shuttering mechanism.
Figure 14B:
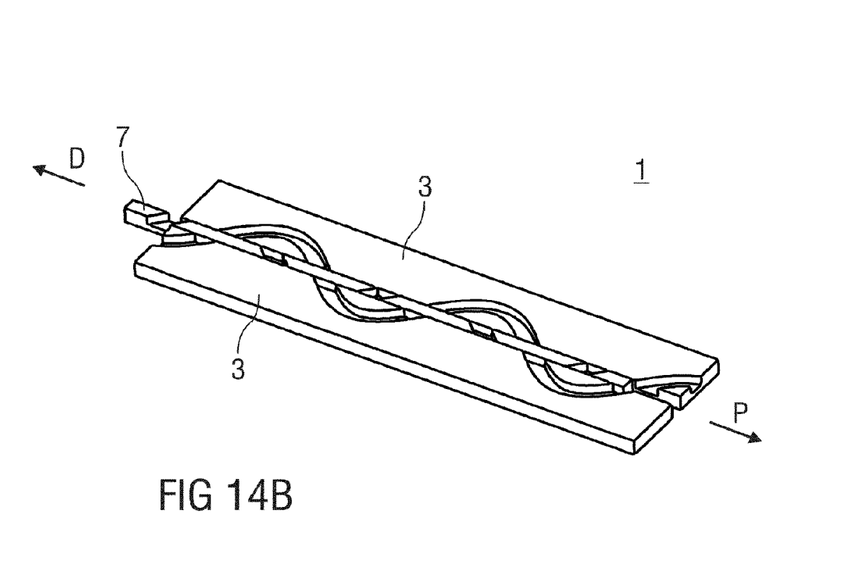

In yet another embodiment the dog 6 could oscillate through a continuous sinusoidal path cut into the two shutters 3, 7 (see FIGS. 13 and 14). The sinusoidal path would be broken by shifting the moving shutter 7 into the locking position thus preventing the dog 6 from advancing beyond the next change-over between the shutters 3, 7.

The invention claimed is:

1. An auto-injector for administering a dose of a liquid medicament, the auto-injector having a distal end and a proximal end with an orifice intended to be applied against an injection site and comprising:
    an elongate housing arranged to contain a syringe with a hollow needle and a stopper for sealing the syringe and displacing the medicament, wherein the syringe is slidably arranged with respect to the housing,
    a drive capable of, upon activation:
    pushing the needle from a retracted position into an advanced position through the orifice and past the proximal end, and
    operating the syringe to supply the dose of medicament,
    a plunger for transmitting power from the drive to at least one of the syringe and the stopper,
    a plunger arm attached to the plunger and comprising a dog, and
    a shuttering mechanism arranged to lock the drive in a compressed state prior to manual operation and capable of, upon manual operation, releasing the drive for injection, the shuttering mechanism further being arranged to control translation of the plunger and comprising:
    a fixed shutter attached to the housing and comprising a fixed protrusion, the fixed protrusion arranged to engage the dog of the plunger arm to prevent translation of the plunger in a proximal direction, the dog of the plunger arm being resiliently biased toward the fixed shutter, and
    a moving shutter arm arranged alongside the fixed shutter and moveable between a locking position and an unlocking position, the moving shutter arm comprising a moving protrusion with a ramp, the moving shutter arm being configured to:
    disengage the dog from the fixed protrusion when the moving shutter arm is moved to the locking position and the dog is engaged to the fixed protrusion, and
    enable the dog to engage with the fixed protrusion when the moving shutter arm is in the unlocking position.

2. The auto-injector of claim 1, further comprising a sheath telescoped within a proximal end of the housing, connected to the moving shutter arm, and arranged to protrude proximally from the housing at least in an initial position in an as delivered state of the auto-injector with the moving shutter arm in the locking position,
    wherein the sheath is translatable in a distal direction from an initial position to a triggering position to shift the moving shutter arm into the unlocking position, the sheath being in the initial position in an as-delivered state of the auto-injector in which the moving shutter is in the locking position.

3. The auto-injector of claim 1, wherein the moving shutter arm is further configured to prevent the dog from engaging the fixed protrusion when the moving shutter arm is in the locking position.

4. The auto-injector of claim 1, wherein the fixed shutter is integrated with the housing.

5. The auto-injector of claim 1, wherein the moving shutter arm is arranged to be translated along a longitudinal axis of the housing between its locking position and its unlocking position.

6. The auto-injector of claim 1, wherein the moving shutter arm is arranged to be rotated about a longitudinal axis of the housing between its locking position and its unlocking position.

7. The auto-injector of claim 1, wherein the fixed shutter comprises a plurality of fixed protrusions spaced from each other, a most distal fixed protrusion of the plurality of fixed protrusions being arranged as a castellation and the other fixed protrusions comprising ramps facing in a distal direction.

8. The auto-injector of claim 1, wherein:
    the fixed shutter comprises a plurality of fixed protrusions in the shape of castellations spaced from each other and protruding to a first side of the housing,
    the moving shutter arm comprises a moving protrusion protruding to a second side of the housing opposite the first side, the moving protrusion comprising a ramp engageable with a ramp in the fixed shutter to cause the moving shutter arm to move relative to the fixed shutter such that a backside of the moving shutter arm becomes substantially flush with a top of the plurality of fixed protrusions to disengage the dog from the fixed shutter or prevent them from re-engaging.

9. The auto-injector of claim 1, wherein:
    the fixed shutter comprises a plurality of fixed protrusions spaced from each other,
    the moving shutter arm comprises a plurality of moving protrusions spaced from each other, and
    the plurality of fixed protrusions and the plurality of moving protrusions comprise substantially corresponding pitches.

10. The auto-injector of claim 9, wherein the plurality of fixed protrusions are arranged as castellations.

11. The auto-injector of claim 9, wherein:
    a most distal moving protrusion comprises a ramp, and
    the other moving protrusions are arranged as castellations.

12. The auto-injector of claim 9, wherein the plurality of moving protrusions comprise ramps facing in substantially one direction.

13. The auto-injector of claim 12, wherein the plurality of fixed protrusions comprise ramps facing in a direction opposite the one direction of the ramps of the plurality of moving protrusions.

14. The auto-injector of claim 12, wherein the ramp of a most distal moving protrusion of the plurality of moving protrusions is longer than the ramps of the other moving protrusions.

15. The auto-injector of claim 12, wherein the ramp of a most distal moving protrusion of the plurality of moving protrusions is steeper than the ramps of the other moving protrusions.

16. The auto-injector of claim 12, wherein the shuttering mechanism comprises at least two fixed shutters and at least two moving shutters arranged as pairs with pitches of the pairs out of phase with each other.

* * * * *